United States Patent
Yuan et al.

(10) Patent No.: US 9,890,371 B2
(45) Date of Patent: Feb. 13, 2018

(54) THERMOPHILIC ETHANOL-RESISTANT β-GLUCOSIDASE AND ENCODING GENE AND APPLICATION THEREOF

(71) Applicant: GUANGZHOU INSTITUTE OF ENERGY CONVERSION, CHINESE ACADEMY OF SCIENCES, Guangzhou, Guangdong (CN)

(72) Inventors: Zhenhong Yuan, Guangzhou (CN); Cuiyi Liang, Guangzhou (CN); Jingliang Xu, Guangzhou (CN); Xiaoyan Chen, Guangzhou (CN); Xinshu Zhuang, Guangzhou (CN); Yu Zhang, Guangzhou (CN); Ying Guo, Guangzhou (CN); Weizheng Zhou, Guangzhou (CN)

(73) Assignee: GUANGZHOU INSTITUTE OF ENERGY CONVERSION, CHINESE ACADEMY OF SCIENCES, Guangdong (CN)

( * ) Notice: Subject to any disclaimer, the term of this patent is extended or adjusted under 35 U.S.C. 154(b) by 0 days.

(21) Appl. No.: 14/892,002

(22) PCT Filed: Oct. 9, 2014

(86) PCT No.: PCT/CN2014/088168
§ 371 (c)(1),
(2) Date: Nov. 18, 2015

(87) PCT Pub. No.: WO2015/180362
PCT Pub. Date: Dec. 3, 2015

(65) Prior Publication Data
US 2016/0362669 A1 Dec. 15, 2016

(30) Foreign Application Priority Data

May 29, 2014 (CN) .......................... 2014 1 0235451

(51) Int. Cl.
*C12N 15/81* (2006.01)
*C12N 15/70* (2006.01)
(Continued)

(52) U.S. Cl.
CPC ............. *C12N 9/2445* (2013.01); *C12N 1/16* (2013.01); *C12N 1/20* (2013.01); *C12N 15/70* (2013.01);
(Continued)

(58) Field of Classification Search
None
See application file for complete search history.

(56) References Cited

U.S. PATENT DOCUMENTS

2004/0203095 A1* 10/2004 Muller ................. C12N 9/6427
435/69.1

FOREIGN PATENT DOCUMENTS

CN 102559511 A * 7/2012 ............... C12N 1/14

OTHER PUBLICATIONS

GenBank Accession No. EHK42488.1, published Nov. 29, 2011.*
(Continued)

*Primary Examiner* — Richard Ekstrom
(74) *Attorney, Agent, or Firm* — Westerman, Hattori, Daniels & Adrian, LLP

(57) ABSTRACT

The present invention discloses thermophilic ethanol-resistant β-glucosidase and an encoding gene and application thereof. The amino acid sequence of the thermophilic ethanol-resistant β-glucosidase of the present invention is as shown in SEQ ID NO: 2, and the nucleotide sequence of the encoding gene is as shown in SEQ ID NO: 1. The nature of the thermophilic ethanol-resistant β-glucosidase of the present invention is conductive to the application of cellulose high-temperature simultaneous saccharification and fermentation, the enzyme has a relatively high enzyme activity and
(Continued)

obvious active effect, cellobiose is kept at low concentration level during the whole fermentation period, the inhibition of terminal products can be effectively eliminated, the thermophilic ethanol-resistant β-glucosidase can be applied on the process of fuel ethanol production, and the important application value of the thermophilic ethanol-resistant β-glucosidase of the present invention in the aspect of bioenergy is further indicated.

8 Claims, 4 Drawing Sheets

(51) Int. Cl.
    *C12N 15/75*     (2006.01)
    *C12N 1/16*     (2006.01)
    *C12N 1/20*     (2006.01)
    *C12N 9/42*     (2006.01)
    *C12P 7/10*     (2006.01)

(52) U.S. Cl.
    CPC ............ *C12N 15/75* (2013.01); *C12N 15/815* (2013.01); *C12P 7/10* (2013.01); *C12Y 302/01021* (2013.01); *Y02E 50/16* (2013.01)

(56) References Cited

OTHER PUBLICATIONS

Machine English Translation of the abstract, description and claims of CN102559511A, published Jul. 11, 2012.*

Hong et al., "Cloning and functional expression of thermostable beta-glucosidase gene from Thermoascus aurantiacus", Applied Microbiology and Biotechnology, vol. 73, pp. 1331-1339, 2007.*

Kawai et al., "Production and characterization of recombinant Phanerochaete chrysosporium beta-glucosidase in the methylotrophic yeast Pichia psastoris", Bioscience, Biotechnology, and Biochemistry, vol. 67, No. 1, pp. 1-7, 2003.*

Schmoll et al., "Cloning of genes expressed early during cellulase induction in Hypocrea jecorina by a rapid subtraction hybridization approach", Fungal Genetics and Biology, vol. 41, pp. 877-887, 2004.*

Takashima et al., "Molecular cloning an expression of the novel fungal beta-glucosidase genes from Humicola grisea and Trichoderma reesei", Journal of Biochemistry, vol. 125, pp. 728-736, 1999.*

* cited by examiner

A          B

THERMOPHILIC ETHANOL-RESISTANT β-GLUCOSIDASE AND ENCODING GENE AND APPLICATION THEREOF

FIELD OF THE INVENTION

The invention belongs to the field of enzyme gene engineering and enzyme engineering and specifically relates to thermophilic ethanol-resistant β-glucosidase and an encoding gene and application thereof.

BACKGROUND OF THE INVENTION

β-Glucosidase (EC3. 2. 1, 21) belongs to the class of cellulose hydrolases and is one kind of enzyme, which can used for hydrolysis or transferring β-1,4-glycosidic bonds. The β-glucosidase is an important constituent in cellulase system. No less than three kinds of enzymes, namely endoglucanase, cellobiohydrolase and β-glucosidase are needed for the cellulose conversion into glucose. Cellulose can be degraded into cellobiose by endoglucanase and cellobiohydrolase, and further decomposed into glucose by β-glucosidase. Releasing of glucose from cellobiose is the key rate-limiting step for the cellulose hydrolysis.

However, the content of β-glucosidase in cellulase system is very low, which is less than 1%, and the activity is generally relatively low, which is a main bottleneck for cellulose enzymatic conversion. For a long time, the poor enzymes properties, low yields of the enzymes and low specific activity of the enzymes are main bottlenecks on their actual application. Although β-glucosidase widely exists in nature, fungi, bacteria and other microbes have low enzyme production efficiency, are difficult to obtain quantities of β-glucosidase, and still have relatively poor thermostability. At present, the activity of β-glucosidase can not meet the needs of industrial production yet, and the cost is further relatively high. In the saccharification process of cellulose, the most appropriate action temperature of the cellulase is about 50° C. generally, while the most appropriate temperature for yeast fermentation is about 30° C. How to coordinate the temperature of the two processes is the key for efficiently producing ethanol by simultaneous saccharification and fermentation (SSF), and one of the methods for solving the contradiction is using a thermophilic yeast instead of traditional yeast. Thus, cloning and expression of β-glucosidase genes have been one of important links on cellulose studies. So far, β-glucosidase genes have been cloned from hundreds of microbes, and many β-glucosidase genes from microbes are heterologously expressed. In recent years, gene engineering technology was used to construct recombinant microorganisms to secret and express β-glucosidases with high activity and thermal stability, which is a research hotspot in the field of cellulose studies.

The known patents and literature reports of thermophilic β-glucosidase and the genes thereof are as follows: β-glucosidase gene fragment BCC2871 from *Periconia* sp. reported by Piyanun Harnpicharnchai, et al., [Protein Expres Purif, 67: 61-69, 2009]; β-glucosidase gene Cel3a from thermophilic fungal *Talaromyces emersonii* reported by Patrick Murraya, et al., [Protein Expres Purif, 38: 248-257, 2004]; β-glucosidase gene PtBglu3 from *Paecilomyces thermophila* reported by Qiaojuan Yan, et al., [Protein Expres Purif, 84: 64-72, 2012]; β-glucosidase gene BglC from *Thermobifida Fusca* reported by Xiao-Qiong Pei et al., [Bioresour. Technol., 102: 3337-3342, 2011]; and DSM 50691 thermophilic β-glucosidase gene Tt-bgl from *Thermotoga thermarum* reported by Linguo Zhao, et al., [J Mol Catal B-Enzym, 95: 62-69, 2013] and so on. There are a variety of types of β-glucosidase produced by microbes, and β-glucosidases from different, sources showed different characteristics. Due to different industrial applications, the β-glucosidase with new properties needs to be developed continuously for being better applicable to the industrial production needs. Wherein, thermophilic enzymes have peat advantages, including higher reaction rate, long-time reaction stability low pollution possibility and strengthen the tolerance to chemical reagents, and high enzyme activities under the required special conditions and so on. So the development of thermophilic β-glucosidase has become the research hotspot.

In our previous studies, we obtained two strains of strains producing β-glucosidase: *Trichoderma viride* W2 with patent number of ZL 201010577713.6 and *Hypocrea* sp. W63 with patent number of ZL 201110417104.9, both of them showed thermophilic and ethanol-resistant properties. Wherein the optimal pH value of the *Trichoderma viride* W2 is 4.8, the optimal temperature is 70° C. The activity of β-glucosidase can be largely improved by 1.6 times at 10% (v/v) of ethanol concentration, which is stable below 30% (v/v) of ethanol concentration; and the optimal pH value of *Hypocrea* sp. W63 is 4.8, the optimal temperature is 65° C., and the concentration of ethanol at 10% (v/v) also has the greatest effect of promoting on enzyme activity, which can improve the enzyme activity of β-glucosidase by nearly 1 time and the highest ethanol resistance concentration also is 30% (v/v).

Under normal circumstances, the cellulose produced by fungi mainly comprises endoglucanase and cellobiohydrolase, and the content of β-glucosidase in the cellulose system is the lowest, which is less than 1%. Many kinds of enzyme produced by gene engineering strain have the advantages of high genetic stability, rapid enzyme production, high enzyme yield and so on, and the produced recombinant enzymes are intended to meet the demands of future industrial applications. According to worldwide reports, the gene cloning of thermophilic β-glucosidases were mainly focused on cloned from thermophilic bacteria and fungi. However, the β-glucosidase produced by the thermophilic microbes do not have thermophilicity and thermal stability necessarily. As for β-glucosidases producing, microbes *Trichoderma* is one of the species researched most extensively before, but there are no report about β-glucosidase genes with thermophilic ethanol-resistant performance, which are cloned from *Hypocrea* sp.

SUMMARY OF THE INVENTION

The first purpose of the present invention is to provide thermophilic ethanol-resistant β-glucosidase and an encoding gene thereof.

The thermophilic ethanol-resistant β-glucosidase of the present invention, wherein the amino acid sequence is as shown in SEQ ID NO: 7.

A gene encoding the thermophilic ethanol-resistant β-glucosidase of the present invention, wherein the thermophilic ethanol-resistant β-glucosidase with the amino acid sequence as shown in SEQ ED NO: 2 is encoded.

Preferably, the nucleotide sequence of the gene encoding the thermophilic ethanol-resistant β-glucosidase is as shown in SEQ ID NO: 1.

*Hypocrea* sp. W63 (ZL201110417104.9) produces the thermophilic ethanol-resistant β-glucosidase, the enzyme has the specificity of hydrolyzing a 4-nitrophenyl β-D-glucopyranoside (pNPG) substrate, the optimal pH value is 4.8, the optimal temperature is 65° C. and the concentration of ethanol in the reaction is 10% (v/v), thereby having the greatest effect of promoting the enzyme activity, improving enzyme activity of the β-glucosidase by nearly 1 time and enabling the ethanol tolerance to be as high as 30% (v/v).

The present invention obtains thermophilic ethanol-resistant β-glucosidase gene epB-BGL from *Hypocrea* sp. W63, the nucleotide sequence with the length of 2202 bp as shown in SEQ ID NO: 1, and the thermophilic ethanol-resistant β-glucosidase gene encodes a protein consisting of 733 amino acids, and the amino acid sequence is as shown in SEQ ID NO: 2. The present invention obtains a recombinant plasmid which contains a gene fragment and takes pPIC9K as an the expression vector, and *Pichia pastoris* GS115 is used as an expression host, the resulting recombinant strain containing the plasmid above has the ability of secreting the thermophilic ethanol-resistant β-glucosidase gene. Thus, the present invention successfully cloned and heterogenous expressed the thermophilic ethanol-resistant β-glucosidase gene into other host through gene engineering or molecular biological methods, and the thermophilic ethanol-resistant β-glucosidase of the present invention is produced by other host.

Compared with the known β-glucosidase, the thermophilic ethanol-resistant β-glucosidase of the present invention is a novel β-glucosidase with new functions. By sequence analysis on BLAST program, the encoding amino acid sequence of the thermophilic ethanol-resistant β-glucosidase gene of the present invention with other reported amino acid sequences of the β-glucosidase the amino acid sequence as shown in SEQ ID NO: 2 has the highest homology with that of the β-glucosidase from *Trichoderma reesei* (Genbank index number AAA18473.1) with the similarity of the amino acid sequences is 79%, and the β-glucosidases with the similarity higher than 79% is from *Trichoderma atroviride* EMI 206040 (Kubicek, C. P., et al., Genome Biol. 12 (4), R40 (2011), without functional identification); and *Trichoderma virens* Gv29-8 (Kubicek, C. R, et al., Genome Biol. 12 (4), R40 (2011), without functional identification). Those proteins with similarity higher than were performed with sequence identification or protein structure research, it is found that in the strains with the similarity of more than 79%, sequence comparison or research of the protein structures is performed, but so far, no related literature reports about functional characterization of the β-glucosidase genes of the corresponding strains have been found. It can be seen that the thermophilic ethanol-resistant β-glucosidase gene epB-BGL of the present invention is a new gene. The thermophilic ethanol-resistant β-glucosidase of the present invention has submitted the nucleotide sequence into GenBank under the number of 10502670, the nucleotide sequence is as shown in SEQ ID NO: 1.

The second purpose of the invention is to provide a recombinant expression vector, wherein containing the thermophilic ethanol-resistant β-glucosidase gene of the present invention.

Preferably, the recombinant expression vector is a pPIC9K expression vector.

The third purpose of the present invention is to provide a host cell, wherein is a eukaryotic cell or prokaryotic cell contains the recombinant expression vector.

The prokaryotic cell can be various organisms, such as a yeast engineering strain, *Escherichia coli* or *Bacillus subtilis*.

Preferably the yeast engineering strain is *Pichia pastoris* GS115 strain.

The fourth purpose of the present invention is to provide an application of the thermophilic ethanol-resistant β-glucosidase in the production of ethanol from cellulose with process of simultaneous saccharification and fermentation at high-temperature.

By similarity analysis of the amino acid sequences of the enzymes, the known β-glucosidases respectively belongs to glycoside hydrolases families 1 (GH1) and glycoside hydrolases families 3 (GH3). By sequence comparison and analysis of the thermophilic ethanol-resistant β-glucosidase of the present invention, the thermophilic ethanol-resistant β-glucosidase is one member in the GH3 family of the glycoside hydrolases.

In addition, the enzymatic properties of the thermophilic ethanol-resistant β-glucosidase of the present invention are different, from those of the known β-glucosidases; and according to the activity determination of the reaction enzyme activity, the reaction temperature is 40-90° C. and the optimal temperature is 70° C.; the reaction pH value is 4.0-6.5, and the optimal pH value is 5.0; and ethanol can promote the enzyme activity of β-glucosidase when the ethanol concentration is within 30% (v/v) in the reaction system. Wherein when the ethanol concentration is 10-20% (v/v), the β-glucosidase activity was most largely improved by 86.29%. All this properties mentioned above proving that the enzyme has the characteristic of keeping a relatively high enzyme activity in the presence of the ethanol at high temperature. The thermophilic ethanol-resistant β-glucosidase has the theoretical molecular weight of 76740 daltons and the pI of 6.01. The pure enzyme had the highest specific activity of 194.25 U/mg on pNPG. which showed the enzyme can specifically catalyze and hydrolyze β-glycosidic bonds to convert cellobiose into glucose and is a key enzyme in cellulase system. By applying the thermophilic ethanol-resistant β-glucosidase of the present invention was applied to the production of ethanol by simultaneous saccharification at high-temperature, biomass raw materials were firstly pre-hydrolyzed, and then an enzyme solution of the thermophilic ethanol-resistant β-glucosidase and thermostability yeast was added for high-temperature simultaneous saccharification and fermentation, so that the inhibition of cellobiose can be effectively eliminated and the yield of the ethanol was improved by 39%. Under the most appropriate conditions for enzymolysis of the cellulose enzyme and fermentation of the yeast in the process for producing the fuel ethanol from the raw material of cellulose by simultaneous saccharification and fermentation, the enzyme kept a relatively high enzyme activity and can be applied to produce fuel ethanol, so the thermophilic ethanol-resistant β-glucosidase of the present invention has an important application value in the aspect of bioenergy.

DETAILED DESCRIPTION OF THE EMBODIMENTS

Figure 1:
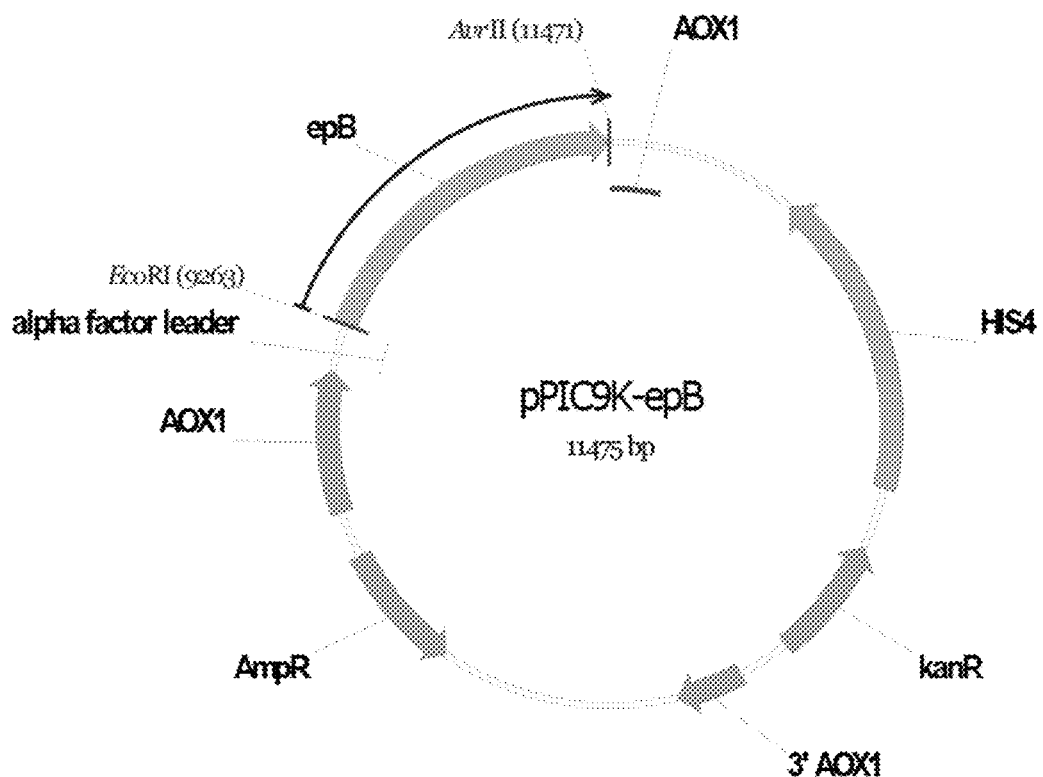
FIG. 1 is a construction pattern diagram of a recombinant plasmid pPIC9K.

The following, embodiments are used for further describing the invention rather than limiting the invention.

Materials used in the embodiments of the invention comprise: fungal total RNA fast extraction kit (purchased from Sangon Biotech Co., Ltd.); cDNA first strand synthesis kit (purchased from Thermo Company); *Pichia pastoris* GS115 and primer synthesis (purchased from Invitrogen Company); pPIC9K expression vector (purchased from Invitrogen Company); competent cell Trans-T1 and pEASY-Blunt Zero Cloning Kit (purchased from TransGen Biotech); PCR reagent, restriction endonuclease EcoRI, AvrII, SalI and T4 DNA ligase (purchased from Takara Company), cellulase compel (purchased from Genencor Company) and thermostability yeast NCYC587 (purchased from UK National Collection of Yeast Cultures); and *Hypocrea* sp. W63, collected in the China General Microbiological Culture Collection Center (CGMCC) on Sep. 1, 2011, with the collection number of CGMCC No. 5209 (the strain is published in Chinese Patent No. 201110417104.9).

The preparation of *P. pastoris* GS115 competent cell is known in the prior art.

Embodiment 1: Cloning of Thermophilic Ethanol-Resistant β-Glucosidase Gene of the Present Invention 1. Extraction of Total RNA of *Hypocrea* sp. W63

Early studies have proved that β-glucosidase produced by *Hypocrea* sp. W63 has thermophilic ethanol-resistant enzymatic performances, maintained high enzyme activity in the presence of ethanol at high temperature and is different from the known β-glucosidase. Thus, in the embodiment, a fungal total RNA fast extraction kit was used for extracting RNA of *Hypocrea* sp. W63 and the specific operation steps were as follows:

(1) Taking 450 μL of Buffer Rlysis-F and adding into a 1.5 mL RNase-free centrifugal tube for later use;
(2) Taking a fresh culture, centrifugally collecting thalli, fully grinding 0.1 g of mycelia in liquid nitrogen, transferring into a 1 mL centrifugal tube, mentioned in (1) immediately shaking and uniformly mixing, and placing at room temperature for 5 min;
(3) Adding 0.2 mL of chloroform into the pyrolysis sample of (2) and uniformly mixing by a vortex oscillator; and centrifuging at 4° C. and 12000 g for 5 min, and carefully sucking out supernatant fluid;
(4) Transferring the supernatant fluid to a 1.5 mL RNase-free centrifugal tube, adding ½ volume of anhydrous ethanol and fully and uniformly mixing;
(5) Putting an adsorption column into a collection tube, completely adding the solution of (4) into the adsorption column with a pipette, standing for 1 min, centrifuging at 12000 g for 1 min, and pouring away waste liquid in the collection tube;
(6) Respectively adding 3 μL of 10×DNase I Buffer; 1.5 μL of Recombinant DNase I (5 U/μL); 1.5 μL of RNase Inhibitor (40 U/μL); and 24 μL of DEPC-treated water, reacting at the temperature of 37° C. for 20-30 min and removing DNA interference;
(7) Adding 500 μL of GT Solution into the adsorption column, standing for 1 min, centrifuging at 10000 g for 1 min and pouring away the waste liquid in the collection tube;
(8) Putting the adsorption column into the collection tube, adding 500 μL of NT Solution, standing for 1 min, centrifuging at 10000 g for 1 min and pouring away the waste liquid in the collection tube;
(9) Putting the adsorption column into the collection tube, centrifuging at 12000 g for 2 min, and opening a cover for several minutes (Volatilizing the residual ethanol); and
(10) Putting the adsorption column into a new 1.5 mL RNase-free centrifugal tube, adding 30-50 μL of DEPC-treated water, standing for 2 min, centrifuging at 12000 g for 2 min and putting the obtained RNA at −70° C. for cryopreservation.

2. cDNA Cloning of Thermophilic Ethanol-Resistant β-Glucosidase Gene of the Present Invention Seven amino acid sequences with relatively high similarity of β-glucosidase were searched in GenBank database, then Multiple Sequence Alignment in DNAman software was used for homologous comparison of these sequences, and the design of a pair of primers $P_1$ and $P_3$ was performed according to two highly conserved sequences and the known sequences of the homologous β-glucosidase genes. A cDNA first strand synthesis kit was adopted for cDNA synthesis. PCR amplification was performed to obtain cDNA sequence, using 1 μL of the above total RNA solution as a template for reverse transcription of cDNA connection and $P_1$ and $P_3$ primer set as follow.

$P_1$:
5-WSN ATH TGG GAY ACN TT-3

$P_3$:
5-CC NAR YTG YTT NCK CAT-3

Touchdown PCR

Reaction conditions were as follows: pre-denaturation at 94° C. for 3 min; then 10 cycles as follows: denaturating at 94° C. for 30 s; annealing at 60-45° C. for 30 s; extending at 72° C. for 30 s; then another 25 cycles: denaturating at 94° C. for 30 s; annealing at 45° C. for 30 s; extending at 72° C. for 30 s, and performing 25 cycles; and finally extending at 72° C. for 6 min. 1% agarose gel electrophoresis was performed to detect whether a target gene with an appropriate size exists or not. Then, target gene with the size of about 1.8 kb was obtained and preserved at −20° C. for further study.

Figure 2:
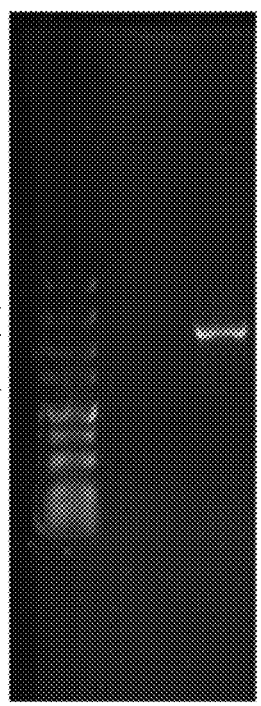
FIG. 2 is gel electrophoresis analysis of thermophilic ethanol-resistant β-glucosidase cDNA of the present invention, wherein M lane is Marker, and lane 1 is cDNA of a target gene.

The specific primers were designed according to the comparison of the known sequences, and the PCR reaction was performed. The reaction procedure was as follows: pre-denaturation at 94° C. for 5 min; then cycling as follows:

denaturating at 94° C. for 30 s; annealing at 52° C. for 30 s; extending at 72° C. for 30 s and performing 30 cycles; and finally extending at 72° C. for 10 min. 1% agarose gel electrophoresis analysis was performed for the PCR product analysis. Connection, transformation, identification and sequencing of the target gene fragment were performed. The fall-length cDNA with the size of about 2.2 kb of the target gene (as shown in FIG. 2) was obtained.

The obtained sequence was analyzed by using BLAST on NCBI, the encoding gene of the thermophilic ethanol-resistant β-glucosidase was confirmed, which was named as epB-BGL. The correct open-reading frame was constituted of 2202 bp nucleotides; and the thermophilic ethanol-resistant β-glucosidase gene epB-BGL encoded the protein containing 733 amino acids, and DNAstar software was used for predicting to get the results that the theoretical molecular weight of the protein was 76550.45 daltons and the isoelectric point was 6.01. The β-glucosidase from *Trichoderma reesei* (Genbank index number A.A.A18473.1) had the highest homology with a catalytic functional domain of the epB-BGL gene, and the similarity between the amino acid sequences was 79%. The nucleotide sequence of the thermophilic ethanol-resistant β-glucosidase gene epB-BGL of the present invention has been submitted the nucleotide sequence on GenBank and the sequence number ID is KJ502670.

Embodiment 2: Expression of β-Glucosidase of the Present Invention in *Pichia pastoris* GS115 and Purification 1. Construction of an epB-BGL Gene Expression Plasmid According to the obtained full-length cDNA sequence of the thermophilic ethanol-resistant β-glucosidase, a pair of expression primers ep3 and ep5 were designed, the predict signal peptide sequence and 3' and 5' non-encoding region sequences were removed, and EcoRI and AvrII enzyme digestion sites were introduced into the two ends of upstream and downstream primers respectively to ensure directional insertion of the epB-BGL gene into vector pPIC9K. The spacing interval between the two primers was about 2.5 kb, and amplification products contained mature protein encoding sequences of the thermophilic ethanol-resistant β-glucosidase.

```
ep3:
5-'CGGAATTCATGCTTTACACAGCCGTAGCG-3' ep5:
5'-CCCCTAGGCTATGAGACCGTGAAGCTTCC-3'
```

The amplification full-length cDNA PCR product of the thermophilic ethanol-resistant β-glucosidase was taken as the template, and the ep5 and the ep3 were taken as the upstream and downstream primers for performing PCR thereby obtaining the gene expression sequence of the mature peptide of the thermophilic ethanol-resistant β-glucosidase. After the target gene was recovered, a pEASY-Blunt Zero Cloning Kit was used for connecting the target fragment with the pPIC9K expression vector, and transformed into *Escherichia coli* Trans-T1 competent cell for propagation, Positive clones were screened by colony PCR and enzyme digestion identification of the plasmid DNA, sequencing was performed, and the plasmid which was sequenced and identified correctly was named as pPIC9K-epB.

Figure 3:
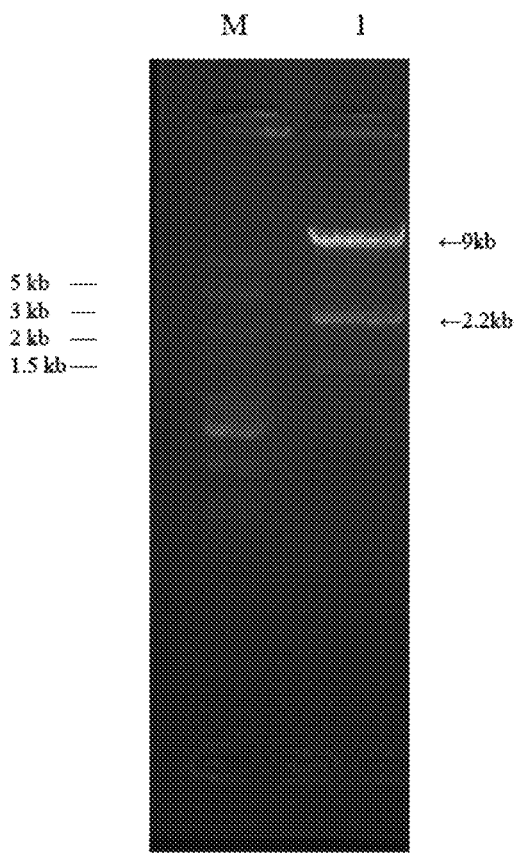
FIG. 3 is an EcoRI and AvrII double enzyme digestion electrophoresis analysis of a cloned plasmid pPIC9K-epB of thermophilic ethanol-resistant β-glucosidase of the present invention, wherein M lane is Marker, and lane 1 is EcoRI and AvrII double enzyme digestion of the plasmid pPIC9K-epB.

EcoRI and AvrII were used for double enzyme digestion of the plasmid pPIC9K-epB which was sequenced and verified to contain a correct reading frame of the thermophilic ethanol-resistant β-glucosidase gene, the inserted fragment was recovered, the connection with the yeast expression plasmid pPIC9K which was also subjected to double enzyme digestion was performed by T4 DNA ligase, the *Escherichia coli* competent cell Trans-T1 was transformed, the transformed Trans-T1 was subjected to ampicillin resistance screening, the colony was subjected to culture at 37° C. overnight with shaking, then the plasmid was extracted, the recombinant plasmid was subjected to enzyme digestion identification and sequencing, the enzyme digestion identification result was as shown in FIG. 3, the recombinant plasmid was named as pPIC9K-epB and the construction pattern diagram was as shown in FIG. 1.

2. Expression of the Recombinant Plasmid pPIC9K-epB in *Pichia pastoris* GS115 and Purification Sal I restriction enzyme (positioned in a His4 region) was used for performing lining of the recombinant plasmid pPIC9K-epB, the same performance was carried out on empty pPIC9K vector plasmid as positive control.

Yeast Transformation and Screening:
(1) Preparing *P. pastoris* GS115 competent cell;
(2) Transforming *P. pastoris* GS115 competent cell by electric shock with the recombinant expression plasmid pPIC9K-epB, wherein the specific steps of the electrical control method were as follows:
a) Uniformly mixing 10 µL of linear DNA and 80 µL of thalli obtained in step (1) and transferring into a 0.2 cm pre-cooled electric transformation cup;
b) Putting electric transformation cup on ice for ice-bathing for 5 min;
c) Performing electric shock for 4-5 msec according to a yeast transformation program built in the electric transformation cup under the conditions that the voltage was 1.5-1.8 kV, the capacitance was 25 µF and the resistance was 200Ω; and
d) Immediately adding 1 mL of 1M sorbitol solution into the electric, transformation cup after the completion of the electric shock, uniformly mixing the thalli, transferring into a new EP tube, uniformly coating the thalli on an MD flat plate, culturing at 30° C. till the appearance of the single colony, observing the size of the colony, counting and screening the transformants with plump shape on the MD flat plate.
(3) Correspondingly inoculating the yeast transformants onto a fresh MD flat plate with sterile disposable toothpick, performing inverted culture at 30° C. for 2-4 d, and preserved in glycerine.

Culture of the Yeast Engineering Strain and Induction of Secretion and Expression of the Thermophilic Ethanol-Resistant β-Glucosidase:
(1) Selecting the positive colony, inoculating into a 250 mL shaking flask containing 25 mL of BMGY culture medium and performing shaking culture at 28-30° C. (250-300 rpm) till the logarithmic growth phase (OD600 value of 2-6, about 16-18 h), thereby taking the GS115 strain harboring pPIC9K empty vector as the control;
(2) Centrifuging at 3000 g at room temperature for 5 min to recover yeast cells, abandoning supernatant, re-suspending the cells in an appropriate volume of BMMY culture medium, culturing till the OD600 value is 1.0-2.0 (about 100-200 mL), then putting a culture solution into a 500 mL shaking flask, covering eight layers of sterile gauze, putting into a shaking table, continuously culturing at 28-30° C. and starting to induce the expression (note: the induction temperature should be strictly controlled and should not exceed 30° C.);

(3) After the starting of the induction of the expression, replenishing 100% of methanol every 24 h till the final concentration was 1% to maintain the induction; and (4) Inducing the expression for 5 d, taking the fermentation supernatant, centrifuging at 4° C. and 12000 rpm and performing detection and analysis on the enzyme activity of an expression product.

Figure 4:
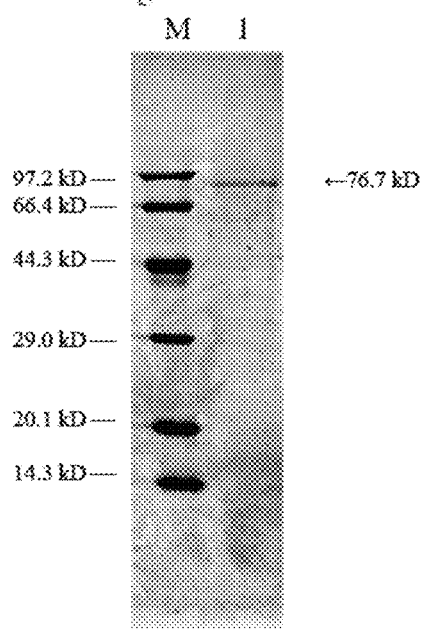
FIG. 4 is a SDS-PAGE analysis of purification of thermophilic ethanol-resistant β-glucosidase expressed by *P. pastoris* GS115, wherein M lane is Marker, and lane 1 is Micro-Prep DEAE column purification.
Figure 5:
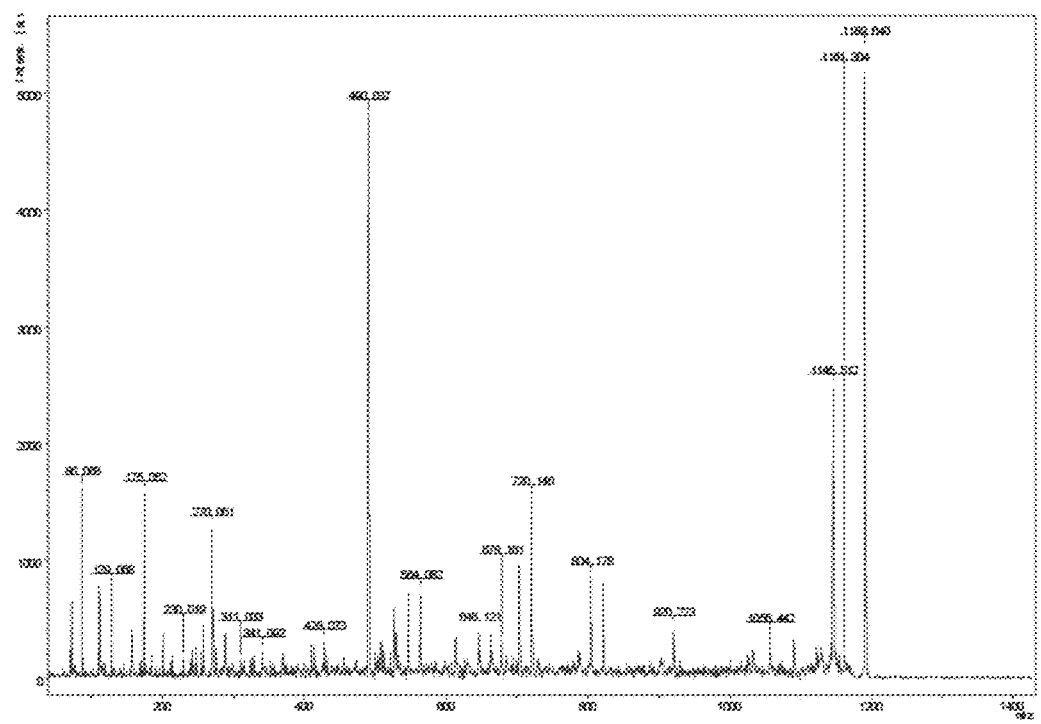
FIG. 5 is mass spectrometry analysis of thermophilic ethanol-resistant β-glucosidase protein of the present invention.

Purification of the Expression Product of the Thermophilic Ethanol-Resistant β-Glucosidase Engineering Strain:

precipitating an extracted crude enzyme solution with ammonium sulfate with the saturation degree of 90% for 4 h, then centrifuging at 4 and 14000 rpm for 20 min, collecting a precipitate, re-dissolving with an appropriate amount of buffer solution A (20 mmol/L of Tris-HCl buffer solution, pH 7.0), applying the solution to a desalting column pre-equilibrated by buffer solution A, collecting 2 mL of a peak appeared at A280 nm, applying an enzyme solution collected after desalting to a Micro-Prep DEAE column pre-equilibrated by the buffer solution A, firstly eluting an enzyme protein with 3 times the column volume of the buffer solution A till the A280 was constant, and further performing gradient elution with 5 times of the buffer solution A (20 mmol/L of Tris-HCl buffer solution, pH 7.0) and a buffer solution B (1 mol/L of Tris-HCl buffer solution, pH 7.0), wherein the flow rate was 1 mL/min and 1 mL was collected for each tube. The determination of enzyme activity and the determination of protein concentration were performed on each tube the SDS-PAGE electrophoresis purity detection was finally performed (the result was as shown in FIG. 4), and the highest specific activity of the enzyme after purification was 194.25 U/mg. After SDS-PAGE electrophoresis, gel cutting recovery was performed, protein spectrum identification and analysis were performed on the target protein, the tandem MS (MS/MS) determined molecular weight of the enzyme was 76740 daltons, which was similar to the theoretically calculated molecular weight (76550 daltons), the MS results was as shown in FIG. 5.

Embodiment 3: Enzymatic Properties of Thermophilic Ethanol-Resistant β-Glucosidase of the Present Invention The enzyme activity of the thermophilic ethanol-resistant β-glucosidase of the present invention was determined as follows: using 4-nitrophenyl β-D-glucopyranoside (pNPG) as substrate, total reaction whim is 2 mL, firstly uniformly mixing 1 mL of pNPG (5 mmol/L) and 0.9 mL of $Na_2HPO_4$-citric acid buffer solution with the pH of 5.0, further adding 0.1 mL of appropriately diluted thermophilic ethanol-resistant β-glucosidase preparation obtained in the previous step, incubating at 50° C. for 10 min, immediately adding 3 mL of $Na_2CO_3$ solution of 1 mol/L to terminate the reaction, placing at room temperature for 5 min and determining the absorbance at 400 nm (OD).

The definition of the enzyme activity was as follows: the amount for catalyzing the production of 1 μmol/L of p-nitrophenol within 1 min was defined as one enzyme unit.

The determination of the enzymatic properties of the thermophilic ethanol-resistant β-glucosidase was as follows: performing enzyme activity determination reaction on the β-glucosidase preparation according to a pNPG determination method by regulating the buffer solution with different pH values, different temperatures and different ethanol concentrations under the situation that the other conditions are constant, wherein the conditions under which the highest enzyme activity was determined to be 100% were the relative activity for determining the thermophilic ethanol-resistant β-glucosidase.

Figure 6:
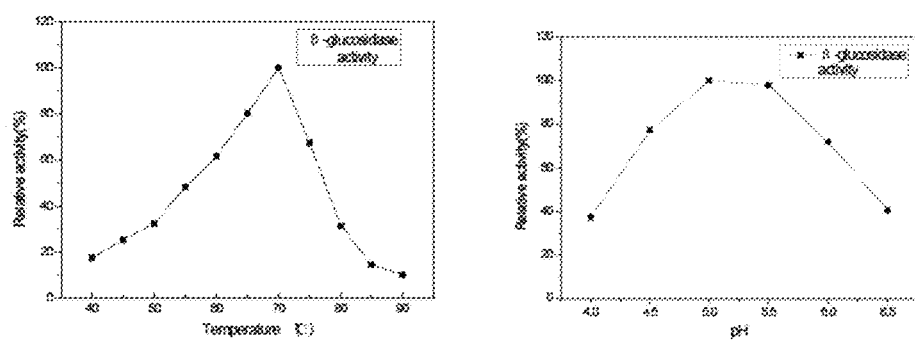
FIG. 6 shows optimal reaction temperature and pH value of thermophilic ethanol-resistant β-glucosidase of the present invention.
Figure 7:
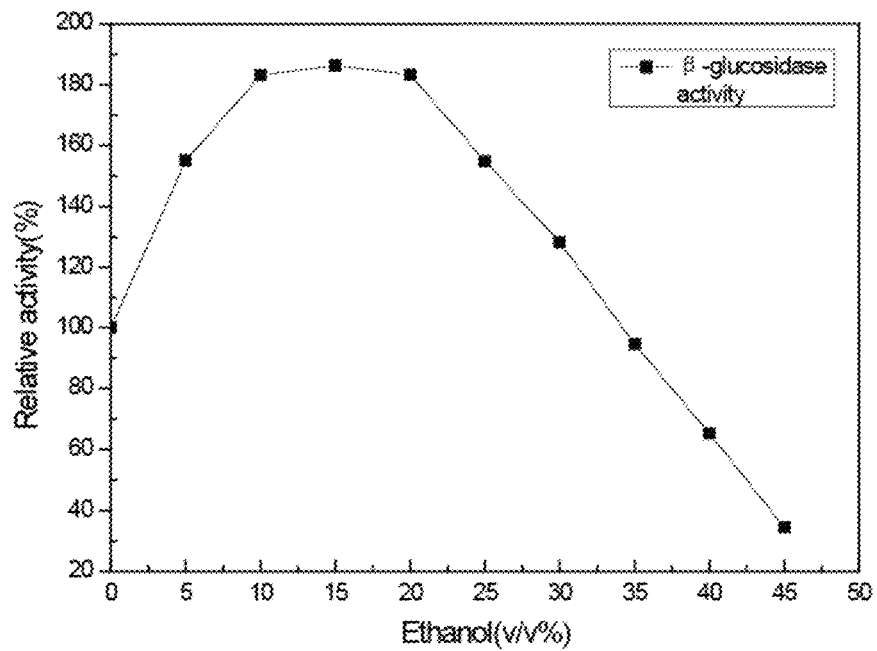
FIG. 7 shows the effects of addition of ethanol on enzyme activity of thermophilic ethanol-resistant β-glucosidase of the present invention.

The thermophilic ethanol-resistant β-glucosidase of present invention kept the high enzyme activity at high temperature in the presence of ethanol, the reaction temperature was 40-90° C. and the optimal temperature was 70° C. (as shown in FIG. 6A); the reaction pH value was 4.0-6.5, and the optimal pH value was 5.0-5.5 (as shown in FIG. 6B); and ethanol could promote the enzyme activity of the thermophilic ethanol-resistant β-glucosidase when the concentration of ethanol was within 30% (v/v), wherein when the ethanol concentration in the reaction system was 10-20% (v/v), the effect of promoting the activity of the thermophilic ethanol-resistant β-glucosidase was the strongest, and the activity of the thermophilic ethanol-resistant β-glucosidase was improved by 86.29%.

Embodiment 4: Application of the Thermophilic Ethanol-Resistant β-Glucosidase of the Present Invention to High-Temperature Simultaneous Saccharification and Fermentation (1) Crushing the substrate, namely bagasse to 60 meshes, pretreatment with 2% of NaOH at 80° C. for 2 h, washing with running water till neutral pH and drying at 65° C. till constant weight;

(2) Culturing the thermostability yeast NCYC587 with a YM liquid culture medium at 42° C. for 24 h for activation;

(3) Adding 30 FPU/g substrate of cellulase into the reaction system and performing pre-hydrolysis at 50° C. for 24 h;

(4) Further addling 15 FPU/g substrate of the thermophilic ethanol-resistant β-glucosidase preparation into the reaction system, inoculating the yeast into the reaction system according to the inoculation amount of 10%, fermenting at 45° C., sampling at 0 h, 24 h, 48 h, 96 h and 120 h by taking the inoculation of the yeast as 0 h, and performing HPLC detection of the content of ethanol and the content of reducing sugar.

The reaction system was as follows: loading 200 mL of reaction solution into a 500 mL shaking flask, wherein the reaction solution contained 30 g of bagasse after alkali treatment, inorganic salt components, namely 0.5 g/L of $(NH_4)_2HPO_4$, 0.025 g/L of $MgSO_4.7H_2O$, 1.0 g/L of yeast extract and the balance of $Na_2HPO_4$-citric acid buffer solution with the pH of 5.0.

The preparation which was not added with the thermophilic ethanol-resistant β-glucosidase of the invention was taken as the control for researching the effects of thermophilic ethanol-resistant β-glucosidase when being applied to high-temperature simultaneous saccharification and fermentation.

Figure 8:
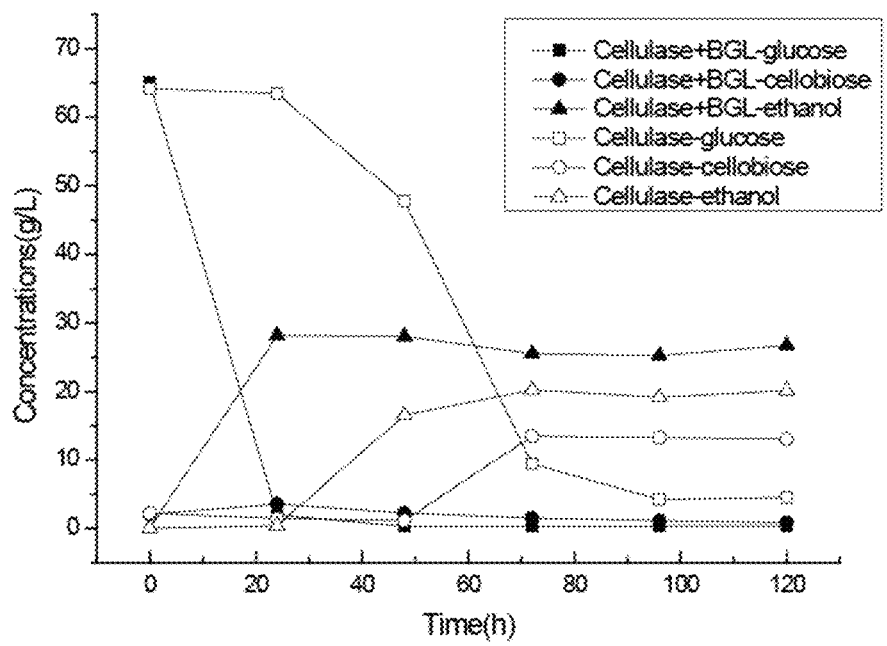
FIG. 8 shows the effects of thermophilic ethanol-resistant β-glucosidase of the present invention on high-temperature simultaneous saccharification and fermentation.

The results were as shown in FIG. 8, when the thermophilic ethanol-resistant β-glucosidase was applied to high-temperature simultaneous saccharification and fermentation, the highest yield of the ethanol could be obtained by fermenting for 24 h, and the content of the produced ethanol was as high as 28.2 g/L, which was improved by 39% in comparison with the yield of the ethanol in the control. Thus, it was clear that the nature of the thermophilic ethanol-resistant β-glucosidase of the invention was conductive to the application of cellulose high-temperature simultaneous saccharification and fermentation was kept at low concentration level during the whole fermentation period, the inhibition of terminal products was effectively eliminated, and under the most appropriate conditions for hydrolysis of the cellulose and fermentation for producing fuel ethanol from the raw material by simultaneous saccharification and fermentation, the enzyme had a relatively high enzyme activity and obvious active effect and could be applied on the process of producing fuel ethanol, indicating that the thermophilic ethanol-resistant β-glucosidase of the invention had an important application value in the aspect of bioenergy.

The above detailed description is only used for specifically describing the feasible embodiments of the invention, the embodiments are not used for limiting the scope of patent of the invention, and equivalent implementations or variations which do not deviate from the invention should be within the scope of the patent of the invention.

Sequence Table

<110> Guangzhou Institute of Energy Conversion, Chinese Academy of Sciences

<120> Thermophilic ethanol-resistant β-glucosidase and encoding gene and application thereof

<160> 2

<210> 1

<211> 2202

<212> DNA

<213> *Hypocrea* sp. W63

<400> 1

| | | | | | |
|---|---|---|---|---|---|
| ATGCTTTACA | CAGCCGTAGC | GGCGTTGGCC | ATTGCCACAA | CGCCCTTTGT | AAGGGCAGGG | 60 |
| AGTGCAGTCA | CTCCTCCAGC | AGGCTCTCCT | TGGGCCACCG | CATATTCCAA | AGCTCAGACG | 120 |
| GCATTGGCCA | AGCTCTCGCT | CCAGGATAAA | GTCGGCATCG | TGACTGGCGT | TGGCTGGAAC | 180 |
| AAGGGGCCCT | GCGTTGGAAA | CACATCTCCA | GCGTCAAGTA | TCAGCTATCC | TCAGTTGTGT | 240 |
| CTTCAAGATT | CACCACTGGG | CATCCGGTTC | TCAACGGGCA | ACACTGCTTT | CACGCCAGGC | 300 |
| GTCCAAGCCG | CCTCAACATG | GGATCTAGAT | TTAATCGGCC | AGCGCGGTCA | ATTCATCGGC | 360 |
| CAGGAGAATA | AAGCCGCAGG | CGTTCACGTC | ACTTTGGGGC | CGGTGGCTGG | GCCGCTAGGA | 420 |
| AAGACGCCAC | AGGGCGGCCG | CAACTGGGAG | GGCTTCAGTC | CCGATCCATA | TCTCACTGGG | 480 |
| TTGGCAATGG | CTGCAACCAT | TAACGGCATT | CAGGGCGCTG | GAGTGCAAGC | AACTGCCAAG | 540 |
| CACTACATCC | TCAACGAGCA | GGAGCTGAAC | CGGGAGAGCA | TGTCCAGCAA | TGCTGACGAC | 600 |
| CGCACCCTTC | ATGAGCTTTA | TGCGTGGCCC | TTTGCCGACG | CCGTAAACGC | CAATGTGGCT | 660 |
| GCCGTCATGT | GCTCGTACAA | CCGAGTCAAT | AGCACGTATG | CGTGTGAGGA | CACGTATACG | 720 |
| CTGCAGACAC | TGCTGAAGAA | CCAGCTGGGA | TTCCCTGGAT | ACGTCATGAC | CGATTGGAAC | 780 |
| GCGCAGCACT | CGACTGTGCA | A4GTGCGCTG | GCAGGTCTCG | ACATGTCGAT | GCCTGGCACT | 840 |
| GACTTCAACG | GTGGCAGCCT | GTACTGGGGA | TCGGCTCTGA | CCAATGCTGT | GAACAGCAAC | 900 |
| CAGGTCCCTC | TGAGCAGGCT | CAATGACATG | GTGACGCGTA | TCCTCGCTGC | GTGGTACTTG | 960 |
| ACGGGCC&IG | ATTCGGGCTT | TCCATCAGTC | AGCTTCAGCA | GGAATGTCCA | GGGAAGTCAC | 1020 |
| AACACCAACG | TACGATCCAT | CGCCAGAGAC | GGCATTGTAC | TTCTCAAGAA | CACCGGCAAT | 1080 |
| ATTCTGCCGC | TGAAAACGCC | GTCGAGCATC | GCCCTCATTG | GATCAGCCAC | CATTGTCGGT | 1140 |
| GCCCACGCAA | ATAACTCGCC | CTCATGCTCT | GACCATCGCT | GCAACCTTGG | TGCCCTCGGA | 1200 |
| ATGGGATGGG | GATCTGGTAC | CGCCAACTAC | CCATACTTTG | TGGCGCCTTA | CGACGCCATC | 1260 |
| AACACAAAGG | CTTCTTCGAT | TGCCGCCAAA | CTGACTCTGA | GCAGTACTGA | TAACACCTCT | 1320 |
| GCTGGCGCGT | CTGCGGCAAG | CGGCAAGGAC | GTTGCCATTG | TCGTCATCAC | TGCAGACTCA | 1380 |
| GGCGAAGGCT | ACATCACTGT | TGAGGGCAAC | GCAGGCGATC | GTAATGACCT | GAACGCATGG | 1440 |

-continued

| Sequence Table |
|---|
| CACAGCGGCA CTGCTCTGGT ACAGGCCGTG GCAGCAGCCA ACAGCAACGT CATCGTCGTT 1500 |
| GTCCACAGTG TCGGCGCCAT TAATCTAGAG CAGATTGTCG CTCTCTCCCA GGTCAAGGCG 1560 |
| ATTGTTTGGG CGGGTCTCCC CTCTCAGGAG AACGGCAATG CGCTGGTCGA TATCCTATGG 1620 |
| GGAGCCATCA GCCCGTCTGG CAAGCTGGTG TATACAATTG CCAAGAGCCC AAGCGACTAT 1680 |
| AACACGCGCA TTTCTTCGGG CGACGACAAC TACAGCGAGG GGCTGTTTAT CGATTACAAG 1740 |
| CACTTTGACG ACGCCGGCAT CACGCCGCGA TACGAGTTCG GCTTTGGACT GGCCTACACA 1800 |
| AACTTTACCT ACTCTGGCCT TTCCATCACC TCAAACGCCA AGTCTGGACC AGCCACCGGC 1860 |
| GCTGTGGTTC CTGGAGGCCC CAGCGATCTG TTCCAGGATG TCGCCACCGT GACTGTGAGC 1920 |
| ATCAAAAACA CTGGAGCCGT GACTGGCGCC GAGGTTGCCC AGCTGTACAT CACCTACCCG 1980 |
| TCCTCTGCAC CCAGAACCCC CGTGAGGCAG CTTCGAGGCT TCGACAAGCT CAGCTTGACG 2040 |
| GCTGCCCAGA GCGAACCGC GACGTTCAAC ATTCGCAAGC GAGATCTGAC CTACTGGAAC 2100 |
| GTGGCGTCGC AGCAGTGGGT GGTGCCGTCG GGGACTTTTG GCGTGAGCGT TGGAGCGAGC 2160 |
| AGCAGAGATT TGCGTTTGAC GGGAAGCTTC ACGGTCTCAT AG 2202 |

<210> 2

<711> 733

<212> pRT

<213> *Hypocrea* sp. W63

<400> 2

```
Met Leu Tyr Thr Ala Val Ala Ala Leu Ala Ile Ala Thr Thr Pro
1               5                   10                  15
Phe Val Arg Ala Gly Ser Ala Val Thr Pro Pro Ala Gly Ser Pro
                20                  25                  30
Trp Ala Thr Ala Tyr Ser Lys Ala Gln Thr Ala Leu Ala Lys Leu
                35                  40                  45
Ser Leu Gln Asp Lys Val Gly Ile Val Thr Gly Val Gly Trp Asn
                50                  55                  60
Lys Gly Pro Cys Val Gly Asn Thr Ser Pro Ala Ser Ser Ile Ser
                65                  70                  75
Tyr Pro Gln Leu Cys Leu Gln Asp Ser Pro Leu Gly Ile Arg Phe
                80                  85                  90
Ser Thr Gly Asn Thr Ala Phe Thr Pro Gly Val Gln Ala Ala Ser
                95                  100                 105
Thr Trp Asp Leu Asp Leu Ile Gly Gln Arg Gly Gln Phe Ile Gly
                110                 115                 120
Gln Glu Asn Lys Ala Ala Gly Val His Val Thr Leu Gly Pro Val
                125                 130                 135
Ala Gly Pro Leu Gly Lys Thr Pro Gln Gly Gly Arg Asn Trp Glu
                140                 145                 150
Gly Phe Ser Pro Asp Pro Tyr Leu Thr Gly Leu Ala Met Ala Ala
                155                 160                 165
Thr Ile Asn Gly Ile Gln Gly Ala Gly Val Gln Ala Thr Ala Lys
                170                 175                 180
His Tyr Ile Leu Asn Glu Gln Glu Leu Asn Arg Glu Ser Met Ser
                185                 190                 195
Ser Asn Ala Asp Asp Arg Thr Leu His Gln Leu Tyr Ala Trp Pro
                200                 205                 210
```

TABLE-continued

Sequence Table

Phe Ala Asp Ala Val Asn Ala Asn Val Ala Ala Val Met Cys Ser
            215                 220                 225

Tyr Asn Arg Val Asn Ser Thr Tyr Ala Cys Glu Asp Thr Tyr Thr
            230                 235                 240

Len Gln Thr Leu Leu Lys Asn Gln Leu Gly Phe Pro Gly Tyr Val
            245                 250                 255

Met Thr Asp Trp Asn Ala Gln His Ser Thr Val Gln Ser Ala Leu
            260                 265                 270

Ala Gly Leu Asp Met Ser Met Pro Gly Thr Asp Phe Asn Gly Gly
            275                 280                 285

Ser Leu Tyr Trp Gly Ser Ala Leu Thr Asn Ala Val Asn Ser Asn
            290                 295                 300

Gln Val Pro Leu Ser Arg Leu Asn Asp Met Val Thr Arg Ile Leu
            305                 310                 315

Ala Ala Trp Tyr Leu Thr Gly Gln Asp Ser Gly Phe Pro Ser Val
            320                 325                 330

Ser Phe Ser Arg Asn Val Gln Gly Ser His Asn Thr Asn Val Arg
            335                 340                 345

Ser Ile Ala Arg Asp Gly Ile Val Leu Leu Lys Asn Thr Gly Asn
            350                 355                 360

Ile Leu Pro Leu Lys Thr Pro Ser Ser Ile Ala Leu Ile Gly Ser
            365                 370                 375

Ala Thr Ile Val Gly Ala His Ala Asn Asn Ser Ala Ser Cys Ser
            380                 385                 390

Asp His Gly Cys Asn Leu Gly Ala Leu Gly Met Gly Trp Gly Ser
            395                 400                 405

Gly Thr Ala Asn Tyr Pro Tyr Phe Val Ala Pro Tyr Asp Ala Ile
            410                 415                 420

Asn Thr Lys Ala Ser Ser Ile Gly Ala Lys Leu Thr Leu Ser Ser
            425                 430                 435

Thr Asp Asn Thr Ser Ala Gly Ala Ser Ala Ala Ser Gly Lys Asp
            440                 445                 450

Val Ala Ile Val Val Ile Thr Ala Asp Ser Gly Gln Gly Tyr Ile
            455                 460                 465

Thr Val Gln Gly Asn Ala Gly Asp Arg Asn Asp Leu Asn Ala Trp
            470                 475                 480

His Ser Gly Thr Ala Leu Val Gln Ala Val Ala Ala Ala Asn Ser
            485                 490                 495

Asn Val Ile Val Val His Ser Val Gly Ala Ile Ala Leu Glu
            500                 505                 510

Gln Ile Val Ala Leu Ser Gln Val Lys Ala Ile Val Trp Ala Gly
            515                 520                 525

Leu Pro Ser Gln Gln Asn Gly Ala Ala Leu Val Asp Ile Leu Trp
            530                 535                 540

Gly Ala Ile Ser Pro Ser Gly Lys Leu Val Tyr Thr Ile Ala Lys
            545                 550                 555

Ser Pro Ser Asp Tyr Asn Thr Arg Ile Ser Ser Gly Asp Asp Asn
            560                 565                 570

Tyr Ser Gln Gly Leu Phe Ile Asp Tyr Lys His Phe Asp Asp Ala
            575                 580                 585

Gly Ile Thr Pro Arg Tyr Gln Phe Gly Phe Gly Leu Ala Tyr Thr

Sequence Table

```
                   590                 595                 600
Asn Phe Thr Tyr Ser Gly Leu Ser Ile Thr Ser Asn Ala Lys Ser
                605                 610                 615
Gly Pro Ala Thr Gly Ala Val Val Pro Gly Gly Pro Ser Asp Leu
                620                 625                 630
Phe Gln Asp Val Ala Thr Val Thr Val Ser Ile Lys Asn Thr Gly
                635                 640                 645
Ala Val Thr Gly Ala Gln Val Ala Gln Leu Tyr Ile Thr Tyr Pro
                650                 655                 660
Ser Ser Ala Pro Arg Thr Pro Val Arg Gln Leu Arg Gly Phe Asp
                665                 670                 675
Lys Leu Ser Leu Thr Ala Gly Gln Ser Gly Thr Ala Thr Phe Asn
                680                 685                 690
Ile Arg Lys Arg Asp Leu Thr Tyr Trp Asn Val Ala Ser Gln Gln
                695                 700                 705
Trp Val Val Pro Ser Gly Thr Phe Gly Val Ser Val Gly Ala Ser
                710                 715                 720
Ser Arg Asp Leu Arg Leu Thr Gly Ser Phe Thr Val Ser ***
                725                 730
```

SEQUENCE LISTING

<160> NUMBER OF SEQ ID NOS: 6

<210> SEQ ID NO 1
<211> LENGTH: 2202
<212> TYPE: DNA
<213> ORGANISM: Hypocrea sp. W63

<400> SEQUENCE: 1

```
atgctttaca cagccgtagc ggcgttggcc attgccacaa cgcccttttgt aagggcaggg      60
agtgcagtca ctcctccagc aggctctcct tgggccaccg catattccaa agctcagacg     120
gcattggcca agctctcgct ccaggataaa gtcggcatcg tgactggcgt tggctggaac     180
aaggggcccct gcgttggaaa cacatctcca gcgtcaagta tcagctatcc tcagttgtgt     240
cttcaagatt caccactggg catccggttc tcaacgggca acactgcttt cacgccaggc     300
gtccaagccg cctcaacatg ggatctagat ttaatcggcc agcgcggtca attcatcggc     360
caggagaata aagccgcagg cgttcacgtc actttgggc cggtggctgg gccgctagga     420
aagacgccac agggcggccg caactgggag ggcttcagtc ccgatccata tctcactggg     480
ttggcaatgg ctgcaaccat taacggcatt cagggcgctg gagtgcaagc aactgccaag     540
cactacatcc tcaacgagca ggagctgaac cgggagagca tgtccagcaa tgctgacgac     600
cgcaccctttc atgagcttta tgcgtggccc tttgccgacg ccgtaaacgc caatgtggct     660
gccgtcatgt gctcgtacaa ccgagtcaat agcacgtatg cgtgtgagga cacgtatacg     720
ctgcagacac tgctgaagaa ccagctggga ttccctggat acgtcatgac cgattggaac     780
gcgcagcact cgactgtgca aagtgcgctg caggtctcg acatgtcgat gcctggcact     840
gacttcaacg gtggcagcct gtactgggga tcggtctga ccaatgctgt gaacagcaac     900
caggtccctc tgagcaggct caatgacatg gtgacgcgta tcctcgctgc gtggtacttg     960
acgggccaag attcgggctt tccatcagtc agcttcagca ggaatgtcca gggaagtcac    1020
```

```
aacaccaacg tacgatccat cgccagagac ggcattgtac ttctcaagaa caccggcaat    1080
attctgccgc tgaaaacgcc gtcgagcatc gccctcattg gatcagccac cattgtcggt    1140
gcccacgcaa ataactcggc ctcatgctct gaccatggct gcaaccttgg tgccctcgga    1200
atgggatggg gatctggtac cgccaactac ccatactttg tggcgcctta cgacgccatc    1260
aacacaaagg cttcttcgat tggcgccaaa ctgactctga gcagtactga taacacctct    1320
gctggcgcgt ctgcggcaag cggcaaggac gttgccattg tcgtcatcac tgcagactca    1380
ggcgaaggct acatcactgt tgagggcaac gcaggcgatc gtaatgacct gaacgcatgg    1440
cacagcggca ctgctctggt acaggccgtg gcagcagcca acagcaacgt catcgtcgtt    1500
gtccacagtg tcggcgccat taatctagag cagattgtcg ctctctccca ggtcaaggcg    1560
attgtttggg cgggtctccc ctctcaggag aacggcaatg cgctggtcga tatcctatgg    1620
ggagccatca gcccgtctgg caagctggtg tatacaattg ccaagagccc aagcgactat    1680
aacacgcgca tttcttcggg cgacgacaac tacagcgagg ggctgtttat cgattacaag    1740
cactttgacg acgccggcat cacgccgcga tacgagttcg gctttggact ggcctacaca    1800
aactttacct actctggcct ttccatcacc tcaaacgcca gtctggacc agccaccggc    1860 gctgtggttc ctggaggccc cagcgatctg ttccaggatg tcgccaccgt gactgtgagc    1920
atcaaaaaca ctggagccgt gactggcgcc gaggttgccc agctgtacat cacctacccg    1980
tcctctgcac ccagaacccc cgtgaggcag cttcgaggct tcgacaagct cagcttgacg    2040
gctggccaga gcgaaccgc gacgttcaac attcgcaagc gagatctgac ctactggaac    2100
gtggcgtcgc agcagtgggt ggtgccgtcg ggacttttg gcgtgagcgt tggagcgagc    2160
agcagagatt tgcgtttgac gggaagcttc acggtctcat ag                      2202
```

<210> SEQ ID NO 2
<211> LENGTH: 733
<212> TYPE: PRT
<213> ORGANISM: Hypocrea sp. W63

<400> SEQUENCE: 2

```
Met Leu Tyr Thr Ala Val Ala Ala Leu Ala Ile Ala Thr Thr Pro Phe
1               5                   10                  15

Val Arg Ala Gly Ser Ala Val Thr Pro Pro Ala Gly Ser Pro Trp Ala
            20                  25                  30

Thr Ala Tyr Ser Lys Ala Gln Thr Ala Leu Ala Lys Leu Ser Leu Gln
        35                  40                  45

Asp Lys Val Gly Ile Val Thr Gly Val Gly Trp Asn Lys Gly Pro Cys
    50                  55                  60

Val Gly Asn Thr Ser Pro Ala Ser Ser Ile Ser Tyr Pro Gln Leu Cys
65                  70                  75                  80

Leu Gln Asp Ser Pro Leu Gly Ile Arg Phe Ser Thr Gly Asn Thr Ala
                85                  90                  95

Phe Thr Pro Gly Val Gln Ala Ala Ser Thr Trp Asp Leu Asp Leu Ile
            100                 105                 110

Gly Gln Arg Gly Gln Phe Ile Gly Gln Glu Asn Lys Ala Ala Gly Val
        115                 120                 125

His Val Thr Leu Gly Pro Val Ala Gly Pro Leu Gly Lys Thr Pro Gln
    130                 135                 140

Gly Gly Arg Asn Trp Glu Gly Phe Ser Pro Asp Pro Tyr Leu Thr Gly
145                 150                 155                 160
```

```
Leu Ala Met Ala Ala Thr Ile Asn Gly Ile Gln Gly Ala Gly Val Gln
                165                 170                 175
Ala Thr Ala Lys His Tyr Ile Leu Asn Glu Gln Glu Leu Asn Arg Glu
                180                 185                 190
Ser Met Ser Ser Asn Ala Asp Asp Arg Thr Leu His Glu Leu Tyr Ala
                195                 200                 205
Trp Pro Phe Ala Asp Ala Val Asn Ala Asn Val Ala Ala Val Met Cys
                210                 215                 220
Ser Tyr Asn Arg Val Asn Ser Thr Tyr Ala Cys Glu Asp Thr Tyr Thr
225                 230                 235                 240
Leu Gln Thr Leu Leu Lys Asn Gln Leu Gly Phe Pro Gly Tyr Val Met
                245                 250                 255
Thr Asp Trp Asn Ala Gln His Ser Thr Val Gln Ser Ala Leu Ala Gly
                260                 265                 270
Leu Asp Met Ser Met Pro Gly Thr Asp Phe Asn Gly Gly Ser Leu Tyr
                275                 280                 285
Trp Gly Ser Ala Leu Thr Asn Ala Val Asn Ser Asn Gln Val Pro Leu
                290                 295                 300
Ser Arg Leu Asn Asp Met Val Thr Arg Ile Leu Ala Ala Trp Tyr Leu
305                 310                 315                 320
Thr Gly Gln Asp Ser Gly Phe Pro Ser Val Ser Phe Ser Arg Asn Val
                325                 330                 335
Gln Gly Ser His Asn Thr Asn Val Arg Ser Ile Ala Arg Asp Gly Ile
                340                 345                 350
Val Leu Leu Lys Asn Thr Gly Asn Ile Leu Pro Leu Lys Thr Pro Ser
                355                 360                 365
Ser Ile Ala Leu Ile Gly Ser Ala Thr Ile Val Gly Ala His Ala Asn
370                 375                 380
Asn Ser Ala Ser Cys Ser Asp His Gly Cys Asn Leu Gly Ala Leu Gly
385                 390                 395                 400
Met Gly Trp Gly Ser Gly Thr Ala Asn Tyr Pro Tyr Phe Val Ala Pro
                405                 410                 415
Tyr Asp Ala Ile Asn Thr Lys Ala Ser Ser Ile Gly Ala Lys Leu Thr
                420                 425                 430
Leu Ser Ser Thr Asp Asn Thr Ser Ala Gly Ala Ser Ala Ala Ser Gly
                435                 440                 445
Lys Asp Val Ala Ile Val Val Ile Thr Ala Asp Ser Gly Glu Gly Tyr
                450                 455                 460
Ile Thr Val Glu Gly Asn Ala Gly Asp Arg Asn Asp Leu Asn Ala Trp
465                 470                 475                 480
His Ser Gly Thr Ala Leu Val Gln Ala Val Ala Ala Ala Asn Ser Asn
                485                 490                 495
Val Ile Val Val His Ser Val Gly Ala Ile Asn Leu Glu Gln Ile
                500                 505                 510
Val Ala Leu Ser Gln Val Lys Ala Ile Val Trp Ala Gly Leu Pro Ser
                515                 520                 525
Gln Glu Asn Gly Asn Ala Leu Val Asp Ile Leu Trp Gly Ala Ile Ser
                530                 535                 540
Pro Ser Gly Lys Leu Val Tyr Thr Ile Ala Lys Ser Pro Ser Asp Tyr
545                 550                 555                 560
Asn Thr Arg Ile Ser Ser Gly Asp Asp Asn Tyr Ser Glu Gly Leu Phe
                565                 570                 575
Ile Asp Tyr Lys His Phe Asp Asp Ala Gly Ile Thr Pro Arg Tyr Glu
```

```
                580             585             590
Phe Gly Phe Gly Leu Ala Tyr Thr Asn Phe Thr Tyr Ser Gly Leu Ser
                595             600             605

Ile Thr Ser Asn Ala Lys Ser Gly Pro Ala Thr Gly Ala Val Val Pro
            610             615             620

Gly Gly Pro Ser Asp Leu Phe Gln Asp Val Ala Thr Val Thr Val Ser
625             630             635             640

Ile Lys Asn Thr Gly Ala Val Thr Gly Ala Glu Val Ala Gln Leu Tyr
                645             650             655

Ile Thr Tyr Pro Ser Ser Ala Pro Arg Thr Pro Val Arg Gln Leu Arg
                660             665             670

Gly Phe Asp Lys Leu Ser Leu Thr Ala Gly Gln Ser Gly Thr Ala Thr
            675             680             685

Phe Asn Ile Arg Lys Arg Asp Leu Thr Tyr Trp Asn Val Ala Ser Gln
            690             695             700

Gln Trp Val Val Pro Ser Gly Thr Phe Gly Val Ser Val Gly Ala Ser
705             710             715             720

Ser Arg Asp Leu Arg Leu Thr Gly Ser Phe Thr Val Ser
                725             730
```

```
<210> SEQ ID NO 3
<211> LENGTH: 17
<212> TYPE: DNA
<213> ORGANISM: Artificial Sequence
<220> FEATURE:
<223> OTHER INFORMATION: P1 primer
<220> FEATURE:
<221> NAME/KEY: MISC_FEATURE
<222> LOCATION: (1)
<223> OTHER INFORMATION: w is a or t/u
<220> FEATURE:
<221> NAME/KEY: MISC_FEATURE
<222> LOCATION: (2)
<223> OTHER INFORMATION: s is g or c
<220> FEATURE:
<221> NAME/KEY: MISC_FEATURE
<222> LOCATION: (3)
<223> OTHER INFORMATION: n is a or g or c or t/u or unknown or other
<220> FEATURE:
<221> NAME/KEY: MISC_FEATURE
<222> LOCATION: (6)
<223> OTHER INFORMATION: h is a or c or t/u
<220> FEATURE:
<221> NAME/KEY: MISC_FEATURE
<222> LOCATION: (12)
<223> OTHER INFORMATION: y is t/u or c
<220> FEATURE:
<221> NAME/KEY: MISC_FEATURE
<222> LOCATION: (15)
<223> OTHER INFORMATION: n is a or g or c or t/u or unknown or other

<400> SEQUENCE: 3
wsnathtggg ayacntt                                              17

<210> SEQ ID NO 4
<211> LENGTH: 17
<212> TYPE: DNA
<213> ORGANISM: Artificial Sequence
<220> FEATURE:
<223> OTHER INFORMATION: P3 primer
<220> FEATURE:
<221> NAME/KEY: MISC_FEATURE
<222> LOCATION: (3)
<223> OTHER INFORMATION: n is a or g or c or t/u or unknown or other
<220> FEATURE:
<221> NAME/KEY: MISC_FEATURE
<222> LOCATION: (5)
```

```
<223> OTHER INFORMATION: r is g or a
<220> FEATURE:
<221> NAME/KEY: MISC_FEATURE
<222> LOCATION: (6)
<223> OTHER INFORMATION: y is t/u or c
<220> FEATURE:
<221> NAME/KEY: MISC_FEATURE
<222> LOCATION: (9)
<223> OTHER INFORMATION: y is t/u or c
<220> FEATURE:
<221> NAME/KEY: MISC_FEATURE
<222> LOCATION: (12)
<223> OTHER INFORMATION: n is a or g or c or t/u or unknown or other
<220> FEATURE:
<221> NAME/KEY: MISC_FEATURE
<222> LOCATION: (14)
<223> OTHER INFORMATION: k is g or t/u

<400> SEQUENCE: 4
ccnarytgyt tnckcat                                                   17

<210> SEQ ID NO 5
<211> LENGTH: 29
<212> TYPE: DNA
<213> ORGANISM: Artifical Sequence
<220> FEATURE:
<223> OTHER INFORMATION: ep3 primer

<400> SEQUENCE: 5
cggaattcat gctttacaca gccgtagcg                                      29

<210> SEQ ID NO 6
<211> LENGTH: 29
<212> TYPE: DNA
<213> ORGANISM: Artificial Sequence
<220> FEATURE:
<223> OTHER INFORMATION: ep5 primer

<400> SEQUENCE: 6
cccctaggct atgagaccgt gaagcttcc                                      29
```

The invention claimed is:

1. A recombinant expression vector, comprising a gene comprising the nucleotide sequence of SEQ ID NO: 1.

2. The recombinant expression vector according to claim 1, wherein the expression vector is pPIC9K.

3. A host cell, comprising:
the recombinant expression vector according to claim 1, wherein the host cell is a eukaryotic cell or prokaryotic cell.

4. A host cell, comprising:
the recombinant expression vector according to claim 2, wherein the host cell is a eukaryotic cell or prokaryotic cell.

5. The host cell according to claim 3, wherein the host cell is a yeast engineering strain, *Escherichia coli* or *Bacillus subtilis*.

6. The host cell according to claim 4, wherein the host cell is a yeast engineering strain, *Escherichia coli* or *Bacillus subtilis*.

7. The host cell according to claim 3, wherein the host cell is *Pichia pastoris* GS115.

8. The host cell according to claim 4, wherein the host cell is *Pichia pastoris* GS115.

* * * * *